United States Patent [19]
Sato et al.

[11] Patent Number: 5,648,526
[45] Date of Patent: Jul. 15, 1997

[54] PROCESS FOR THE PREPARATION OF E-PROSTAGLANDINS

[75] Inventors: Fumie Sato, 1-219, Kugenumahigashi 3-Chome, Fujisawa-shi, Kanagawa 251, Japan; Takehiro Amano, Tokyo, Japan; Kazuya Kameo, Tokyo, Japan; Tohru Tanami, Tokyo, Japan; Masaru Mutoh, Tokyo, Japan; Naoya Ono, Tokyo, Japan; Jun Goto, Tokyo, Japan

[73] Assignees: Taisho Pharmaceutical Co., Ltd.; Fumie Sato, both of Japan

[21] Appl. No.: 256,924
[22] PCT Filed: Feb. 2, 1993
[86] PCT No.: PCT/JP93/00115
§ 371 Date: Jul. 29, 1994
§ 102(e) Date: Jul. 29, 1994
[87] PCT Pub. No.: WO93/16041
PCT Pub. Date: Aug. 19, 1993

[30] Foreign Application Priority Data

Feb. 5, 1992 [JP] Japan ................... 4-020151
Feb. 5, 1992 [JP] Japan ................... 4-020264

[51] Int. Cl.$^6$ ........................... C07C 405/00
[52] U.S. Cl. ........................... 562/503
[58] Field of Search ................... 562/503

[56] References Cited

FOREIGN PATENT DOCUMENTS 5221392  2/1977  Japan.
5874661  5/1983  Japan.
9218472  10/1992 WIPO.
9218473  10/1992 WIPO.

OTHER PUBLICATIONS

The Chemical Society of Japan, No. 9 (1983) pp. 1390–1392.
Chemistry Letters, No. 10, Oct. 1992 pp. 2095–2098.
Kunz, Angew Chem. Int. Ed. Eng. 73 (1) 71 1984.

Primary Examiner—Robert Gerstl
Attorney, Agent, or Firm—Lorusso & Loud

[57] ABSTRACT

Object: To produce E-prostaglandins in a high yield and in a short time with suppressed formation of isomers.

Structure: A process for preparing E-prostaglandins represented by the formula:

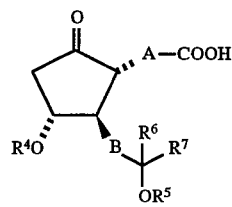

(wherein A, $R^6$ and $R^7$ represent respectively an arbitrary group which does not participate in the reaction; B represents a vinylene or ethynylene group; and $R^4$ and $R^5$ may be the same or different from each other and each represents a hydrogen atom or a protective group of the hydroxyl group) which comprises reacting allyl esters of E-prostaglandins represented by the formula:

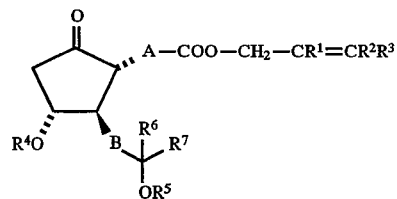

(wherein $R^1$ and $R^2$ may be the same or different from each other and each represents a hydrogen atom or a lower alkyl group; $R^3$ represents a hydrogen atom, a lower alkyl group, an alkenyl group or an aryl group; and A, B, $R^4$, $R^5$, $R^6$ and $R^7$ are as defined above) with at least one substance selected from the group consisting of bases and formic acid in the presence of a zero- or divalent palladium complex or a salt thereof.

10 Claims, No Drawings

PROCESS FOR THE PREPARATION OF E-PROSTAGLANDINS

FIELD OF ART

The present invention relates to a process for preparing E-prostaglandins through the deallylation reaction of allyl esters of E-prostaglandins.

BACKGROUND ART

For the preparation of E-prostaglandins, a method is commonly used in which E-prostaglandins are extracted from the lower alkyl esters of E-prostaglandins. However, since E-prostaglandins are chemically labile and subject to dehydration reaction as they have β-hydroxy-ketone in the skeleton, it is hardly possible to apply the ordinary chemical techniques for their preparation. Hydrolysis by use of an enzyme is known as a most effective method for the preparation of E-prostaglandins (JP-A-52-21392 and A. Hazato et al: Hydrolysis of E-Prostaglandin Methyl Esters Using Esterase, Bul. of Japan Chemical Society, Vol. 9, pp. 1390–1392, 1983).

However, this hydrolytic method using an enzyme has the disadvantage in that a great deal of time is required for the reaction in the case of certain types of E-prostaglandins. Further, in the preparation of E-prostaglandins having the triple bonds at the 13- and 14-positions (the compounds of the formula (II) in which B is ethynylene group), which are among prostaglandings $E_1$, there would be produced the isomers of the objective compound, such as 8-β compounds.

DISCLOSURE OF THE INVENTION

As a result of intensive studies for solving said problems, the present inventors found that when the allyl esters of E-prostaglandins are subjected to a deallylation reaction using a zero- or divalent palladium complex or its salt as catalyst, it is possible to produce the objective E-prostaglandins in a high yield and in a short time with minimized formation of isomers. The present invention has been attained on the basis of this finding.

The present invention provides a process for preparing E-prostaglandins represented by the following formula:

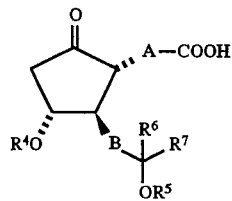

(wherein A, $R^6$ and $R^7$ are each an arbitrary group which does not participate in the reaction; B is a vinylene or ethynylene group; and $R^4$ and $R^5$ may be the same or different from each other and each represents a hydrogen atom or a protective group of the hydroxyl group) which comprises reacting the allyl esters of E-prostaglandins represented by the following formula:

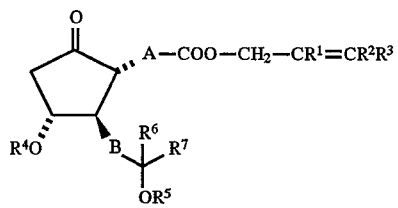

(wherein $R^1$ and $R^2$ may be the same or different from each other and each represents a hydrogen atom or a lower alkyl group; $R^3$ represents a hydrogen atom, a lower alkyl group, an alkenyl group or an aryl group; and A, B, $R^4$, $R^5$, $R^6$ and $R^7$ are as defined above) with at least one substance selected from the group consisting of bases and formic acid in the presence of a zero- or divalent palladium complex or its salt.

In the present invention, the typical examples of the groups represented by the formula $—CH_2—CR^1=CR^2R^3$ (wherein $R^1$, $R^2$ and $R^3$ represent the same as defined above) include those of the following formulae:

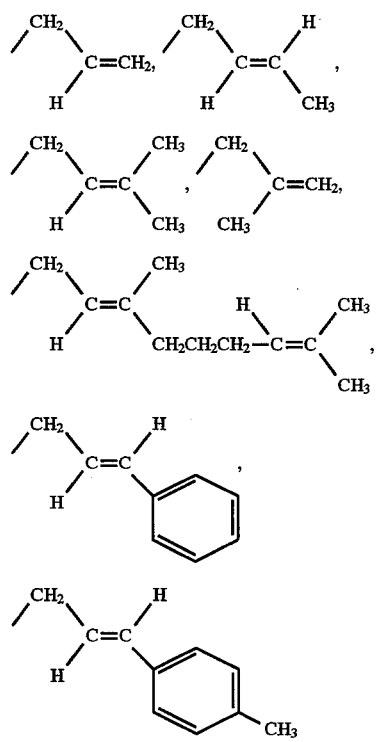

The protective group of the hydroxyl group may be any of those commonly used in the preparation of prostaglandins. Examples of such protective groups include t-butyldimethylsilyl group, triethylsilyl group, phenyldimethylsilyl group, t-butyldiphenylsilyl group, tetrahydropyranyl group, tetrahydrofuranyl group, methoxymethyl group, ethoxyethyl group and benzyl group.

A, $R^6$ and $R^7$ may each be any suitable group which does not participate in the reaction in the process of the present invention. For example, A may be a straight-chain $C_{3-8}$ alkylene group (such as trimethylene group, tetramethylene group, hexamethylene group, octamethylene group, etc.), a straight-chain $C_{3-9}$ alkenylene group [such as the groups represented by the following formulae:

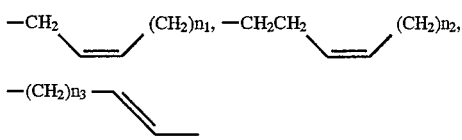

(wherein $n_1$ is an integer of 1 to 6; $n_2$ is an integer of 2 to 5; and $n_3$ is an integer of 1 to 6)], a straight-chain $C_{2-8}$ alkylene group having one oxygen or sulfur atom as intermediary in the molecular chain [such as the groups represented by the following formulae:

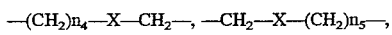

(wherein X is an oxygen or sulfur atom; $n_4$ is an integer of 1 to 6; and $n_5$ is an integer of 1 to 5)], a group represented by the following formula:

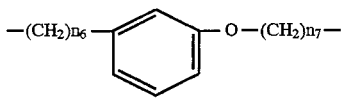

(wherein $n_6$ and $n_7$ may be the same or different from each other and each represents an integer of 1 to 3)], a group represented by the following formula:

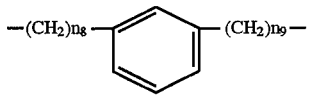

(wherein $n_8$ and $n_9$ may be the same or different from each other and each represents an integer of 1 to 3)], or a straight-chain $C_{3-8}$ alkynylene group (which is excluded in case of using formic acid in the preparation of the compounds of the formula (II)) [such as the groups represented by the following formula:

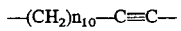

(wherein $n_{10}$ is an integer of 1 to 6)].

Of these compounds, those having the double bonds at the 2- and 3-positions, which fall in the category of prostaglandin $E_1$, are especially noted for their prominent effect of reducing the reaction time.

$R^6$ may be, for example, hydrogen atom, methyl group, ethyl group or vinyl group.

$R^7$ may be, for example, a straight-chain, branched or cyclic $C_{1-10}$ alkyl or alkenyl group (such as pentyl group, hexyl group, 1-methylhexyl group, 2-methylhexyl group, 1,1-dimethylhexyl group, cyclopentyl group, cyclohexyl group, 2-pentenyl group, 5-hexenyl group, etc.), a straight-chain or branched $C_{1-10}$ alkynyl group [which is excluded in case of using formic acid in the preparation of the compounds of the formula (II)] (such as 1-methyl-3-hexenyl group, 2-methyl-3-hexenyl group, 2-pentynyl group, etc.), a $C_{1-4}$ alkyl group substituted with a phenyl group, phenoxy group or $C_{5-6}$ cycloalkyl group (such as cyclopentylmethyl group, cyclohexylmethyl group, 2-cyclopentylethyl group, 3-cyclopentylpropyl group, 3-cyclohexylpropyl group, 4-cyclopentylbutyl group, benzyl group, phenoxymethyl group, 2-phenylethyl group, 4-phenylbutylgroup), or a phenyl group.

The zero- or divalent palladium complexes or salts thereof usable in the reaction include tris(dibenzylideneacetone) dipalladium (0) chloroform, bis(dibenzylideneacetone) palladium (0), tetrakis(triphenylphosphine)palladium (0), bis(acetylacetonate)palladium (II), dichlorobis(benzonitrile) palladium (II), dichlorobis(acetonitrile)palladium (II), dichlorobis(triphenylphosphine)palladium (II), π-allylpalladium (II) chloride complex, palladium chloride, lithium tetrachloropalladate and palladium acetate. Of these palladium complexes and salts thereof, the zero-valent ones are preferred. In the reaction according to the present invention, such palladium complex or salt thereof is used in an amount of 0.01 to 0.5 equivalent to the compound of the formula (I).

The bases usable for the reaction according to the present invention are the organic amines such as triethylamine, tributylamine, diethylamine, diisopropylamine, ethylamine, propylamine, butylamine, piperidine, pyrrole, pyrrolidine, morpholine, N-methylmorpholine, o-methylethanolamine, aniline, dimethylaniline, piperadine, hydrazine, ethylhydrazine, 1,1-dimethylhydrazine, phenylhydrazine, 4-(trimethylsilyl)morpholine, trimethylsilyldiethylamine, trimethylsilyldimethylamine, etc., and ammonia. The base is used in an amount of 1 to 10 equivalents to the compound of the formula (I) used as starting material.

In case of using formic acid, its amount used is one equivalent to excess over the compound of the formula (I).

In the present invention, it is recommended to add a phosphine to the reaction system excepting the case where a phosphine is already coordinated in the "zero- or divalent palladium complex or its salt". The phosphines usable in this invention include triethylphosphine, tributylphosphine, triphenylphosphine, tri(p-tolueneoxy)phosphine, triethoxyphosphine, bis(diphenylphosphino)ethane, bis (diphenylphosphino)propane, bis(diphenylphosphino) butane, and bis(diphenylphosphino)ferrocene.

It is also possible to add, as desired, a solvent [an ether (such as dioxane, tetrahydrofuran, tetrahydropyran, diethyl ether, diethylene glycol dimethyl ether, etc.), an ester (such as ethyl acetate, methyl acetate, valerolactone, etc.), an amide (such as N,N-dimethylformamide, N-methylpyrrolidone, etc.), dimethyl sulfoxide, etc.]

The reaction temperature is from 0° C. to the reflux temperature of the solvent used, preferably from room temperature to 100° C.

Of the compounds of the formula (II) produced according to the process of the present invention, those having the hydroxyl group protected (the compounds of the formula (II) wherein $R^4$ and $R^5$ are a group or groups other than hydrogen atom) can be easily deprotected by a conventional method and made into a prostaglandin E compound (or a derivative thereof) which is useful for the treatment of various kinds of diseases such as peripheral circulatory trouble.

POTENTIALITY OF INDUSTRIAL UTILIZATION

The present invention has made it possible to produce E-prostaglandins in a high yield and in a short time. Also, in the preparation of E-prostaglandins having the triple bonds at the 13- and 14-positions, which are among prostaglandins El, it has become possible to suppress formation of the isomers such as 8-β compounds.

BEST MODE FOR CARRYING OUT THE INVENTION

The present invention is further illustrated by showing the examples.

PREPARATION EXAMPLE 1

Preparation of (2E,17S)-17,20-dimethyl-2,3-didehydro-PGE$_1$ allyl ester 11,15-bis(t-butyldimethylsilyl ether)

A tetrahydrofuran solution (8.98 ml) of copper cyanide(I) dilithium chloride (1.56 g, 8.98 mmol) was added to (4E)-5-carbo[(prop-2'-enyl)oxy]pent-4-enylzinc (II) iodide (0.55M tetrahydrofuran solution, 19.58 ml, 10.77 mmol) at −70° C. and stirred at the same temperature for 15 minutes. To this solution was added a diethyl ether solution (14 ml) of (3R,4R)-2-methylene-3-[(1'E,3'S,5'S)-3'-(t-butyldimethylsiloxy)-5'-methylnon-1'-enyl]-4-(t-butyldimethylsiloxy)-cyclopentan-1-one (1.775 g, 3.59 mmol) and trimethylsilyl chloride (0.82 ml, 6.46 mmol), and the mixed solution was heated to room temperature with stirring over a period of about 2 hours. To the reaction solution was added a saturated aqueous ammonium chloride solution (60 ml), followed by extraction with n-hexane. The organic layer was washed with a saturated saline solution, then dried and concentrated. The residue was dissolved in ether-isopropyl alcohol (1:4, 20 ml), and after adding pyridinium p-toluenesulfonate (46 mg, 0.18 mmol), the solution was stirred at room temperature for 12 hours. To the reaction solution were added ether (50 ml) and a saturated aqueous sodium bicarbonate solution (20 ml). After extraction of this solution, the organic layer was dried and concentrated and the residue was subjected to silica gel column chromatography (n-hexane:ether =4:1) to give the objective compound (1.79 g).

$^1$H-NMR (CDCl$_3$, 300 MHz) δ (ppm): 0.02 and 0.05 (2s, 12H), 0.87 and 0.89 (2s, 18H), 0.70–1.00 (m, 6H), 1.02–1.81 (m, 15H), 1.85–2.03 (m, 1H), 2.08–2.25 (m, 3H), 2.44 (dt, J=10.7 Hz, 7.2 Hz, 1H), 2.63 (dd, J=6.9 Hz, 18.2 Hz, 1H), 3.98–4.09 (m, 1H), 4.11–4.25 (m, 1H), 4.63 (d, J=5.0 Hz, 2H), 5.15–5.40 (m, 2H), 5.45–5.64 (m, 2H), 5.82(d, J=15.4 Hz, 1H), 5.87–6.13 (m, 1H), 6.97 (dt, J=15.4 Hz, 6.6 Hz, 1H).

$^{13}$C-NMR (CDCl$_3$, 75 MHz) δ (ppm): 215.7, 166.1, 149.4, 136.3, 132.4, 128.9, 121.0, 117.9, 73.2, 71.1, 64.7, 53.5, 53.2, 47.5, 46.3, 36.9, 32.0, 29.23, 29.17, 28.2, 27.5, 26.4, 25.9, 25.8, 23.1, 20.0, 18.2, 18.0, 14.2, −4.2, −4.6, −4.67, −4.71.

IR (neat) cm$^{-1}$: 2930, 2855, 1740, 1725, 1650, 1460, 1360, 1250, 1100, 835, 775.

[α]$_D^{21}$=−32.48° (c=1.63, chloroform)

The following compounds were produced by following the procedure of Preparation Example 1. (17R)-17,20-dimethyl-13,14-didehydro-PGE$_1$ allyl ester 11,15-bis(t-butyldimethylsilyl ether)

$^1$H-NMR (CDCl$_3$, 300 MHz) δ (ppm): 0.09, 0.11 and 0.12 (3s, 12H), 0.80–0.94 (m, 6H), 0.86 and 0.89 (2s, 18H), 1.00–1.69 (m, 19H), 2.10–2.24 (m, 1H), 2.17 (dd, J=7.0 Hz, 18.4 Hz, 1H), 2.32 (t, J=7.4 Hz, 2H), 2.60–2.73 (m, 1H), 2.66 (dd, J=6.6 Hz, 18.4 Hz, 1H), 4.20–4.34 (m, 1H), 4.36–4.48 (m, 1H), 4.57 (d, J=5.5 Hz, 2H), 5.17–5.37 (m, 2H), 5.83–6.02 (m, 1H).

(17S)-17,20-dimethyl-13,14-didehydro-PGE$_1$ allyl ester 11,15-bis(t-butyldimethylsilyl ether)

$^1$H-NMR (CDCl$_3$, 300 MHz) δ (ppm): 0.09, 0.11 and 0.12 (3s, 12H), 0.78–0.92 (m, 6H), 0.87 and 0.89 (2s, 18H), 0.98–1.79 (m, 19H), 2.10–2.23 (m, 1H), 2.17 (dd, J=6.7 Hz, 18.0 Hz, 1H), 2.32 (t, J=7.5 Hz, 2H), 2.60–2.73 (m, 2H), 4.20–4.32 (m, 1H), 4.37–4.47 (m, 1H), 4.57 (d, J=5.6 Hz, 2H), 5.18–5.36 (m, 2H), 5.71–6.00 (m, 1H).

(2E,17S)-17,20-dimethyl-2,3,13,14-tetradehydro-PGE$_1$ allyl ester 11,15-bis(t-butyldimethylsilyl ether)

$^1$H-NMR (CDCl$_3$, 300 MHz) δ (ppm): 0.02, 0.11 and 0.12 (3s, 12H), 0.60–1.01 (m, 6H), 0.87 and 0.89 (2s, 18H), 1.01–1.82 (m, 15H), 2.08–2.27 (m, 4H), 2.57–2.73 (m, 2H), 4.22–4.34 (m, 1H), 4.42 (t, J=6.7 Hz, 1H), 4.63 (d, J=5.5 Hz, 2H), 5.15–5.40 (m, 2H), 5.77–6.06 (m, 1H), 5.84 (d, J=15.6 Hz, 1H), 6.98 (dt, J=15.6 Hz, 6.9 Hz, 1H).

(2E,17R)-17,20-dimethyl-2,3,13,14-tetradehydro-PGE$_1$ allyl ester 11,15-bis(t-butyldimethylsilyl ether)

$^1$H-NMR (CDCl$_3$, 300 MHz) δ (ppm): 0.09, 0.11 and 0.12 (3s, 12H), 0.71–1.00 (m, 6H), 0.87 and 0.89 (2s, 18H), 1.00–1.80 (m, 15H), 2.08–2.29 (m, 4H), 2.60–2.73 (m, 2H), 4.22–4.32 (m, 1H), 4.34–4.48 (m, 1H), 4.63 (d, J=5.7 Hz, 2H), 5.19–5.37 (m, 2H), 5.84 (d, J=15.5 Hz, 1H), 5.83–6.01 (m, 1H), 6.98 dt, J=15.5 Hz, 7.0 Hz, 1H).

PREPARATION EXAMPLE 2

Preparation of (2E,17R)-17,20-dimethyl-2,3,13,14-tetradehydro-PGE$_1$ allyl ester 11,15-bis(t-butyldimethylsilyl ether)

A tetrahydrofuran solution (13.6 ml) of copper cyanide(I) dilithium chloride (2.37 g, 13.6 mmol) was added to (4E)-5-carbo[(prop-2'-enyl)oxy]pent-4-enylzinc (II) iodide (0.81M tetrahydrofuran solution, 13.5 ml, 10.9 mmol) at −70° C. and stirred at the same temperature for 15 minutes. To this solution was added a diethyl ether solution of (3R,4R)-2-methylene-3-[(3'S,5'R)-3'-(t-butyldimethylsiloxy)-5'-methylnon-1'-ynyl]-4-(t-butyldimethylsiloxy)-cyclpentan-1-one (2.69 g, 5.45 mmol) and trimethylsilyl chloride (1.25 ml, 9.81 mmol) at −70° C., and the mixed solution was heated to room temperature with stirring over a period of about 2 hours. To the reaction solution was added a saturated aqueous ammonium chloride solution (80 ml), followed by extraction with n-hexane. The organic layer was washed with a saturated saline solution, then dried and concentrated. The residue was dissolved in ether:isopropyl alcohol (1:4, 22 ml), and after adding pyridinium p-toluenesulfonate (68 mg, 0.27 mmol), the solution was stirred at room temperature for 12 hours. To the reaction solution were added ether (50 ml) and a saturated aqueous sodium bicarbonate solution (20 ml). After extraction of the solution, the organic layer was dried and concentrated, and the residue was subjected to silica gel column chromatography (n-hexane: ether=4:1) to give the objective compound (2.52 g).

$^1$H-NMR (CDCl$_3$, 300 MHz) δ ppm: 0.09, 0.11 and 0.12 (3s, 12H), 0.71–1.00 (m, 6H), 0.87 and 0.89 (2s, 18H), 1.00–1.80 (m, 15H), 2.08–2.29 (m, 4H), 2.60–2.73 (m, 2H), 4.22–4.32 (m, 1H), 4.34–4.48 (m, 1H), 4.63 (d, J=5.7 Hz, 2H), 5.19–5.37 (m, 2H), 5.84 (d, J=15.5 Hz, 1H), 5.83–6.01 (m, 1H), 6.98 (dt, J=15.5 Hz, 7.0 Hz, 1H).

The following compound was produced according to the procedure of Preparation Example 2.

(17R)-17,20-dimethyl-13,14-didehydro-PGE$_1$ allyl ester 11,15-bis(t-butyldimethylsilyl ether)

$^1$H-NMR (CDCl$_3$, 300 MHz) δ ppm: 0.09, 0.11 and 0.12 (3s, 12H), 0.80–0.94 (m, 6H), 0.86 and 0.89 (2s, 18H), 1.00–1.69 (m, 19H), 2.10–2.24 (m, 1H), 2.17 (dd, J=7.0 Hz, 18.4 Hz, 1H), 2.32 (t, J=7.4 Hz, 2H), 2.60–2.73 (m, 1H), 2.66 (dd, J=6.6 Hz, 18.4 Hz, 1H), 4.20–4.34 (m, 1H), 4.36–4.48 (m, 1H), 4.57 (d, J=5.5 Hz, 2H), 5.17–5.37 (m, 2H), 5.83–6.02 (m, 1H).

EXAMPLE 1

Preparation of (2E,17S)-17,20-dimethyl-2,3-didehydro-PGE$_1$ 11,15-bis(t-butyldimethylsilyl ether)

Formic acid (0.60 ml, 13.73 mmol), triethylamine (1.64 ml, 11.77 mmol), tris(dibenzylideneacetone)dipalladium(0)

chloroform complex (101.4 mg, 0.10 mmol) and tributylphosphine (98 μl, 0.39 mmol) were mixed and stirred at room temperature for 10 minutes. To this solution was added tetrahydrofuran (20 ml), and after stirring at room temperature for 15 minutes, a tetrahydrofuran solution (20 ml) of (2E,17S)-17,20-dimethyl-2,3-didehydro-PGE$_1$ allyl ester 11,15-bis(t-butyl-dimethylsilyl ether) (2.55 g, 3.92 mmol) produced in Preparation Example 1 was added and stirred at 50° C. for 3 hours. The solution was cooled to room temperature and, after adding a saturated saline solution (40 ml), extracted with n-hexane (40 ml). The organic layer was dried and concentrated and the residue was subjected to silica gel column chromatography (n-hexane:ether=2:1) to give the objective compound (1.275 g).

$^1$H-NMR (CDCl$_3$, 300 MHz) δ (ppm): 0.02 and 0.05 (2s, 12H), 0.87 and 0.89 (2s, 18H), 0.75–0.99 (m, 6H), 1.00–1.88 (m, 15H), 1.90–1.99 (m, 1H), 2.10–2.28 (m, 3H), 2.44 (dt, J=10.7 Hz, 7.1 Hz, 1H), 2.63 (dd, J=6.8 Hz, 18.1 Hz, 1H), 3.98–4.09 (m, 1H), 4.11–4.22 (m, 1H), 5.45–5.62 (m, 2H), 5.81 (d, J=15.7 Hz, 1H), 7.04 (dt, J=15.7 Hz, 6.6 Hz, 1H).

$^{13}$C-NMR (CDCl$_3$, 75 MHz) δ (ppm): 216.2, 172.0, 151.9, 136.4, 128.9, 120.8, 73.3, 71.2, 53.7, 53.3, 47.6, 46.3, 37.0, 32.2, 29.33, 29.27, 28.2, 27.6, 26.5, 26.0, 25.9, 23.2, 20.1, 18.3, 18.1, 14.3, −4.1, −4.5, −4.57, −4.62.

IR (neat) cm$^{-1}$: 3250, 2930, 2855, 1740, 1695, 1645, 1460, 1250, 1100, 835, 775.

$[α]_D^{20}$=−35.08° (c=1.53, chloroform).

The following compounds were produced by following the procedure of Example 1.

(17R)-17,20-dimethyl-13,14-didehydro-PGE$_1$ 11,15-bis(t-butyldimethyl ether

Reaction time: 0.5 hr (50° C.); yield: 78% (no formation of 8-β compounds)

$^1$H-NMR (CDCl$_3$, 300 MHz) δ (ppm): 0.09, 0.11 and 0.12 (3s, 12H), 0.86 and 0.89 (2s, 18H), 0.73–1.02 (m, 6H), 1.02–1.93 (m, 19H), 2.17 (dd, J=18.1 Hz, 7.1 Hz, 1H), 2.06–2.24 (m, 1H), 2.34 (t, J=7.5 Hz, 2H), 2.50–2.72 (m, 2H), 4.22–4.32 (m, 1H), 4.34–4.45 (m, 1H).

(17S)-17,20-dimethyl-13,14-didehydro-PGE$_1$ 11,15-bis(t-butyldimethylsilyl ether)

Reaction time: 11 hr (room temp.); yield: 83% (no formation of 8-β compounds)

$^1$H-NMR (CDCl$_3$, 300 MHz) δ (ppm): 0.09, 0.11 and 0.13 (3s, 12H), 0.69–0.97 (m, 6H), 0.87 and 0.89 (2s, 18H), 1.01–1.89 (m, 19H), 2.17 (dd, J=18.0 Hz, 7.2 Hz, 1H), 2.06–2.23 (m, 1H), 2.34 (t, J=7.5 Hz, 2H), 2.49–2.73 (m, 2H), 4.25–4.36 (m, 1H), 4.36–4.52 (m, 1H).

(2E,17S)-17,20-dimethyl-2,3,13,14-tetradehydro-PGE$_1$ 11,15-bis(t-butyldimethylsilyl ether)

Reaction time: 11 hr (room temp.); yield: 82% (no formation of 8-β compounds)

$^1$H-NMR (CDCl$_3$, 300 MHz) δ (ppm): 0.09, 0.11 and 0.13 (3s, 12H), 0.56–1.00 (m, 6H), 0.87 and 0.89 (2s, 18H), 1.00–1.94 (m, 15H), 2.06–2.30 (m, 4H), 2.58–2.74 (m, 2H), 4.23–4.36 (m, 1H), 4.36–4.47 (m, 1H), 5.82 (d, J=15.6 Hz, 1H), 7.07 (dt, J=15.6 Hz, 7.0 Hz, 1H).

(2E,17R)-17,20-dimethyl-2,3,13,14-tetradehydro-PGE$_1$ 11,15-bis(t-butyldimethylsilyl ether)

Reaction time: 0.5 hr (50° C.); yield: 90% (no formation of 8-δ compounds)

$^1$H-NMR (CDCl$_3$, 300 MHz) δ (ppm): 0.10, 0.11 and 0.13 (3s, 12H), 0.76–1.00 (m, 6H), 0.87 and 0.89 (2s, 18H), 1.00–1.92 (m, 15H), 2.09–2.31 (m, 4H), 2.59–2.72 (m, 2H), 4.21–4.34 (m, 1H), 4.36–4.46 (m, 1H), 5.82 (d, J=15.7 Hz, 1H), 7.06 (dt, J=15.7 Hz, 6.9 Hz, 1H).

EXAMPLE 2

Preparation of (2E,17R)-17,20-dimethyl-2,3,13,14-tetradehydro-PGE$_1$ 11,15-bis(t-butyldimethylsilyl ether)

Tetrakis(triphenylphosphine)palladium (0) (34.7 mg, 0.030 mmol) was added to a solution of (2E,17R)-17,20-dimethyl-2,3-didehydro-PGE$_1$ allyl ester 11,15-bis(t-butyldimethylsilyl ether) (194 mg, 0.30 mmol) produced in Preparation Example 2 and stirred at room temperature for 10 minutes. To this solution was added morpholine (0.130 ml, 1.50 mmol), followed by stirring at room temperature for 20 minutes, further addition of a saturated saline solution (10 ml) and extraction with n-hexane (15 ml). The organic layer was dried and concentrated and the residue was subjected to silica gel column chromatography (n-hexane: ether=9:1) to give the objective compound (135 mg; yield: 74%).

$^1$H-NMR (CDCl$_3$, 300 MHz) δ ppm: 0.10, 0.11 and 0.13 (3s, 12H), 0.76–1.00 (m, 6H), 0.87 and 0.89 (2s, 18H), 1.00–1.92 (m, 15H), 2.09–2.31 (m, 4H), 2.59–2.72 (m, 2H), 4.21–4.34 (m, 1H), 4.36–4.46 (m, 1H), 5.82 (d, J=15.7 Hz, 1H), 7.06 (dt, J=15.7 Hz, 6.9 Hz, 1H).

The following compound was produced according to the procedure of Example 2.

(17R)-17,20-dimethyl-13,14-didehydro-PGE$_1$ 11,15-bis(t-butyldimethylsilyl ether)

Reaction time: same as in Example 2; yield: 78% (no formation of 8-δ compounds)

$^1$H-NMR (CDCl$_3$, 300 MHz) δ ppm: 0.09, 0.11 and 0.12 (3s, 12H), 0.86 and 0.89 (2s, 18H), 0.73–1.02 (m, 6H), 1.02–1.93 (m, 19H), 2.17 (dd, J=18.1 Hz, 7.1 Hz, 1H), 2.06–2.24 (m, 1H), 2.34 (t, J=7.5 Hz, 2H), 2.50–2.72 (m, 2H), 4.22–4.32 (m, 1H), 4.34–4.45 (m, 1H).

EXAMPLE 3

Preparation of (17R)-17,20-dimethyl-2,2,3,3,13,14-hexadehydro-PGE$_1$ 11,15-bis(t-butyldimethylsilyl ether)

Morpholine (0.506 ml, 5.87 mmol) was added to a tetrahydrofuran solution (5 ml) of tris(dibenzilideneacetone) dipalladium (0) chloroform (60.14 mg, 0.058 mmol) and diphenylphosphonopropane (95.67 mg, 0.23 mmol) and stirred at room temperature for 10 minutes. To this solution was added a tetrahydrofuran (5 ml) solution of (17R)-17,20-dimethyl-2,2,3,3,13,14-hexadehydro-PGE$_1$ allyl ester 11,15-bis(t-butyldimethylsilyl ether) (1.248 g, 1.935 mmol) produced according to the process disclosed in WO92/18472, and the mixed solution was stirred at room temperature for 30 minutes and further at 35° C. for 20 minutes. The reaction solution was poured into ether (50 ml) and 1N hydrochloric acid (30 ml), and after separating the liquid, the organic layer was washed with a saturated aqueous sodium hydrogencarbonate solution (30 ml). Then the organic layer was dried over anhydrous magnesium sulfate and filtered, and the filtrate was concentrated in vacuo. The resultant crude product was purified by silica gel column chromatography to give the objective compound (768.4 mg; yield: 66%).

$^1$H-NMR (CDCl$_3$, 300 MHz) δ ppm: 0.01, 0.11 and 0.13 (3s, 12H), 0.89 and 0.90 (2s, 18H), 0.82–0.95 (m, 6H), 1.05–1.84 (m, 15H), 2.12–2.26 (m, 2H), 2.33 (t, J=6.0 Hz, 2H), 2.62–2.74 (m, 2H), 4.24–4.44 (m, 2H)

Rf=0.3 (ether, SiO$_2$).

We claim:

1. A process for preparing an E-prostaglandin represented by the formula:

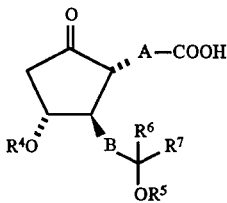

wherein A, $R^6$ and $R^7$ each represent, respectively, an arbitrary group which does not participate in the reaction; B represents a vinylene or ethynylene group; $R^4$ and $R^5$ may be the same or different and each represents a hydrogen atom or a protective group for the hydroxyl, said process comprising reacting an allyl ester of an E-prostaglandin represented by the formula:

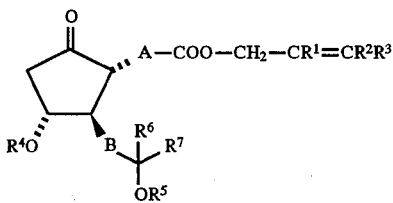

wherein $R^1$ and $R^2$ are the same or different and each represents a hydrogen atom or a lower alkyl group; $R^3$ represents a hydrogen atom, a lower alkyl group, an alkenyl group or an aryl group; and A, B, $R^4$, $R^5$, $R^6$ and $R^7$ are as defined above with at least one reactant selected from the group consisting of bases and formic acid, in the presence of a zero- or divalent palladium complex or a salt thereof.

2. A process according to claim 1, wherein said one reactant is a base in the amount of 1 to 10 equivalents per equivalent of said allyl ester.

3. A process according to claim 2, wherein the palladium complex or salt thereof is used in an amount of 0.01 to 0.5 equivalent per equivalent of said allyl ester.

4. A process according to claim 3, conducted at a temperature of from room temperature to 100° C.

5. A process according to claim 1, wherein said one reactant is formic acid in an amount of at least one equivalent per equivalent of said allyl ester.

6. A process according to claim 5, wherein the palladium complex or salt thereof is used in an amount of 0.01 to 0.5 equivalent per equivalent of said allyl ester.

7. A process according to claim 6, conducted at a reaction temperature of from room temperature to 100° C.

8. A process according to claim 1, wherein said one reactant is a mixture of 1 to 10 equivalents of a base and at least one equivalent of formic acid per equivalent of said allyl ester.

9. A process according to claim 8, wherein the palladium complex or salt thereof is used in an amount of 0.01 to 0.5 equivalent per equivalent of said allyl ester.

10. A process according to claim 9, conducted at a reaction temperature of from room temperature to 100° C.

* * * * *